United States Patent
Kecman et al.

(10) Patent No.: US 8,821,501 B2
(45) Date of Patent: Sep. 2, 2014

(54) PATELLA RESECTIONING GUIDE AND ASSEMBLY

(75) Inventors: Maja Kecman, London (GB); Kyle B. Thomas, Denver, CO (US); Richard A. Hartshorn, London (GB); Edward H. Goodwin, London (GB)

(73) Assignee: DePuy (Ireland), Cork (IE)

( * ) Notice: Subject to any disclaimer, the term of this patent is extended or adjusted under 35 U.S.C. 154(b) by 382 days.

(21) Appl. No.: 13/176,802

(22) Filed: Jul. 6, 2011

(65) Prior Publication Data

US 2012/0078261 A1 Mar. 29, 2012

Related U.S. Application Data

(60) Provisional application No. 61/386,097, filed on Sep. 24, 2010.

(51) Int. Cl.
*A61B 17/58* (2006.01)

(52) U.S. Cl.
USPC .......................................................... 606/88

(58) Field of Classification Search
USPC .......... 606/53, 60, 86 R–105.5 R; 623/20.14, 623/20.18–20.2
See application file for complete search history.

(56) References Cited

U.S. PATENT DOCUMENTS

| | | |
|---|---|---|
| 2,008,011 A | 7/1935 | Foster |
| 3,835,849 A | 9/1974 | McGuire |
| 4,194,861 A | 3/1980 | Keller |
| D260,927 S | 9/1981 | Glenn |
| D281,622 S | 12/1985 | Diamond |
| 4,565,192 A | 1/1986 | Shapiro |
| 4,633,862 A | 1/1987 | Petersen |
| 5,002,547 A | 3/1991 | Poggie et al. |
| 5,021,055 A | 6/1991 | Burkinshaw |
| 5,108,401 A | 4/1992 | Insall et al. |
| 5,116,338 A | 5/1992 | Poggie et al. |
| 5,129,907 A | 7/1992 | Heldreth et al. |
| 5,129,908 A | 7/1992 | Petersen et al. |
| 5,147,365 A | 9/1992 | Whitlock et al. |
| 5,174,693 A | 12/1992 | Lee |
| 5,222,955 A | 6/1993 | Mikhail |
| 5,250,050 A | 10/1993 | Poggie et al. |
| 5,284,482 A | 2/1994 | Mikhail |

(Continued)

FOREIGN PATENT DOCUMENTS

| | | |
|---|---|---|
| EP | 992222 A3 | 4/2000 |
| EP | 1967143 A3 | 7/2013 |

(Continued)

OTHER PUBLICATIONS

European Search Report From Corresponding EPO App. No. 11175824.9-2310, Dated Dec. 16, 2011, 8 Pages.

(Continued)

*Primary Examiner* — Matthew Lawson

(57) ABSTRACT

A patella resection assembly comprises a patella resection guide and a stylus. The patella resection guide has bone-gripping members on two movable arms and a saw guide surface. The stylus is pivotably mounted to the arms of the resection guide and has a free end received in the slot in the resection guide. The arms of the patella resection guide are movable to a variety of positions with different distances between the bone-gripping members while the stylus is in place.

28 Claims, 10 Drawing Sheets

(56) References Cited

U.S. PATENT DOCUMENTS

| | | |
|---|---|---|
| 5,284,485 A | 2/1994 | Kammerer et al. |
| 5,312,409 A | 5/1994 | McLaughlin et al. |
| 5,382,254 A | 1/1995 | McGarry et al. |
| 5,415,663 A | 5/1995 | Luckman et al. |
| 5,470,328 A | 11/1995 | Furnish et al. |
| 5,484,451 A | 1/1996 | Akopov et al. |
| D367,531 S | 2/1996 | Price |
| 5,520,692 A | 5/1996 | Ferrante |
| 5,536,271 A | 7/1996 | Daly et al. |
| 5,542,947 A | 8/1996 | Treacy |
| D373,635 S | 9/1996 | Price |
| 5,575,793 A | 11/1996 | Carls et al. |
| 5,582,615 A | 12/1996 | Foshee et al. |
| 5,593,450 A | 1/1997 | Scott et al. |
| 5,611,802 A | 3/1997 | Samuelson et al. |
| 5,626,607 A | 5/1997 | Malecki et al. |
| 5,667,512 A | 9/1997 | Johnson |
| 5,827,279 A | 10/1998 | Hughett et al. |
| 5,941,884 A | 8/1999 | Corvelli |
| 5,944,723 A | 8/1999 | Colleran et al. |
| 5,968,051 A | 10/1999 | Luckman |
| 6,010,509 A | 1/2000 | Delgado et al. |
| 6,056,754 A | 5/2000 | Haines et al. |
| 6,074,425 A | 6/2000 | Pappas |
| 6,190,391 B1 | 2/2001 | Stubbs |
| 6,205,884 B1 | 3/2001 | Foley et al. |
| D459,474 S | 6/2002 | Bratt et al. |
| 6,419,675 B1 | 7/2002 | Gallo, Sr. et al. |
| D463,550 S | 9/2002 | Sherman |
| 6,855,150 B1 | 2/2005 | Linehan |
| 6,866,667 B2 | 3/2005 | Wood |
| D549,331 S | 8/2007 | Tomatsu et al. |
| 7,344,540 B2 | 3/2008 | Smucker et al. |
| 7,356,902 B2 | 4/2008 | Snider |
| 7,566,335 B1 | 7/2009 | Scott et al. |
| 7,632,279 B2 | 12/2009 | Bastian |
| 7,780,594 B2 | 8/2010 | Hutton |
| 7,806,899 B2 | 10/2010 | Hogg et al. |
| 7,878,989 B2 | 2/2011 | McMinn |
| 7,891,071 B2 | 2/2011 | Collazo |
| D634,011 S | 3/2011 | Phillips et al. |
| D638,541 S | 5/2011 | Claypool |
| 7,972,383 B2 | 7/2011 | Goldstein et al. |
| D642,678 S | 8/2011 | Dockstader et al. |
| D646,389 S | 10/2011 | Claypool et al. |
| 8,216,242 B2 | 7/2012 | Marchyn |
| 2002/0115987 A1 | 8/2002 | Hildwein et al. |
| 2003/0163137 A1 | 8/2003 | Smucker |
| 2004/0153066 A1 | 8/2004 | Coon |
| 2005/0240196 A1 | 10/2005 | Davis |
| 2006/0142777 A1* | 6/2006 | Bastian .......... 606/88 |
| 2007/0118141 A1 | 5/2007 | Marchyn et al. |
| 2007/0162031 A1 | 7/2007 | Hogg |
| 2007/0179626 A1 | 8/2007 | de la Barrera |
| 2007/0233142 A1 | 10/2007 | Oliver |
| 2007/0260227 A1 | 11/2007 | Phan |
| 2008/0097450 A1 | 4/2008 | Brown et al. |
| 2008/0114366 A1 | 5/2008 | Smucker et al. |
| 2008/0177394 A1 | 7/2008 | Chauhan |
| 2008/0228190 A1 | 9/2008 | Sherry et al. |
| 2008/0306484 A1 | 12/2008 | Coon |
| 2009/0264737 A1 | 10/2009 | Haechler et al. |
| 2009/0326661 A1 | 12/2009 | Wright |
| 2010/0030223 A1 | 2/2010 | Keller |
| 2010/0152742 A1 | 6/2010 | Nevelös |
| 2010/0168753 A1 | 7/2010 | Edwards |
| 2010/0204701 A1 | 8/2010 | Tallarida |
| 2011/0066193 A1 | 3/2011 | Lang |
| 2012/0078261 A1 | 3/2012 | Kecman et al. |
| 2013/0023883 A1 | 1/2013 | Wright |
| 2013/0023890 A1 | 1/2013 | Kecman |
| 2013/0030443 A1 | 1/2013 | Wright |
| 2013/0030539 A1 | 1/2013 | Wright |
| 2013/0035693 A1 | 2/2013 | Wright |
| 2013/0079787 A1 | 3/2013 | Jones |
| 2013/0079788 A1 | 3/2013 | Jones |
| 2013/0079789 A1 | 3/2013 | Randle |
| 2013/0211410 A1 | 8/2013 | Landes |

FOREIGN PATENT DOCUMENTS

| | | |
|---|---|---|
| EP | 2574314 B1 | 3/2014 |
| FR | 2737848 A1 | 2/1997 |
| GB | 2433698 A | 7/2007 |
| WO | WO 9945856 A1 | 9/1999 |
| WO | WO 2005110249 A1 | 11/2005 |
| WO | WO 2008112996 A1 | 9/2008 |

OTHER PUBLICATIONS

P.F.C. Sigma Rotating Platform Knee System With M.B.T. Tray, Primary Procedure With a Curved or Posterior Stabilized Implant, 2003, 43 Pages.

LCS High Performance Instruments, Surgical Technique, 2008, 44 Pages.

Sigma High Performance Instruments, Design Rationale, 2007, 12 Pages.

Sigma High Performance Instruments, Classic Surgical Technique, 2010, 52 Pages.

European Search Report, European Patent Application No. 11175824.9-2310, Mar. 1, 2013 (7 pages).

European Search Report for European Application No. 12174682.0-2310, Sep. 5, 2012, 6 pages.

European Search Report for European Application No. 12174683.8-2310, Sep. 3, 2012, 6 pages.

European Search Report for European Application No. 12186675.0-2310, Dec. 12, 2012, 7 pages.

European Search Report for European Application No. 12186700.6-2310, Dec. 13, 2012, 8 pages.

European Search Report for European Application No. 12186728.7-2310, Dec. 14, 2012, 8 pages.

European Search Report for European Application No. 13186416.7-1654 Dec. 6, 2013, 6 pages.

European Search Report, European Pat. App. No. 12191753.8-2310, Jan. 3, 2013 (6 pages).

International Search Report, International Application No. PCT/US12/44947, Oct. 12, 2012, 3 pages.

* cited by examiner

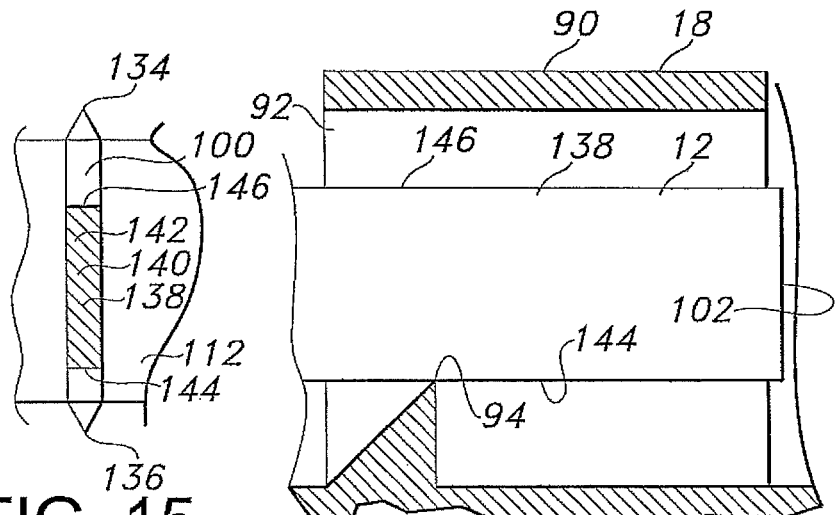
FIG. 15
FIG. 16
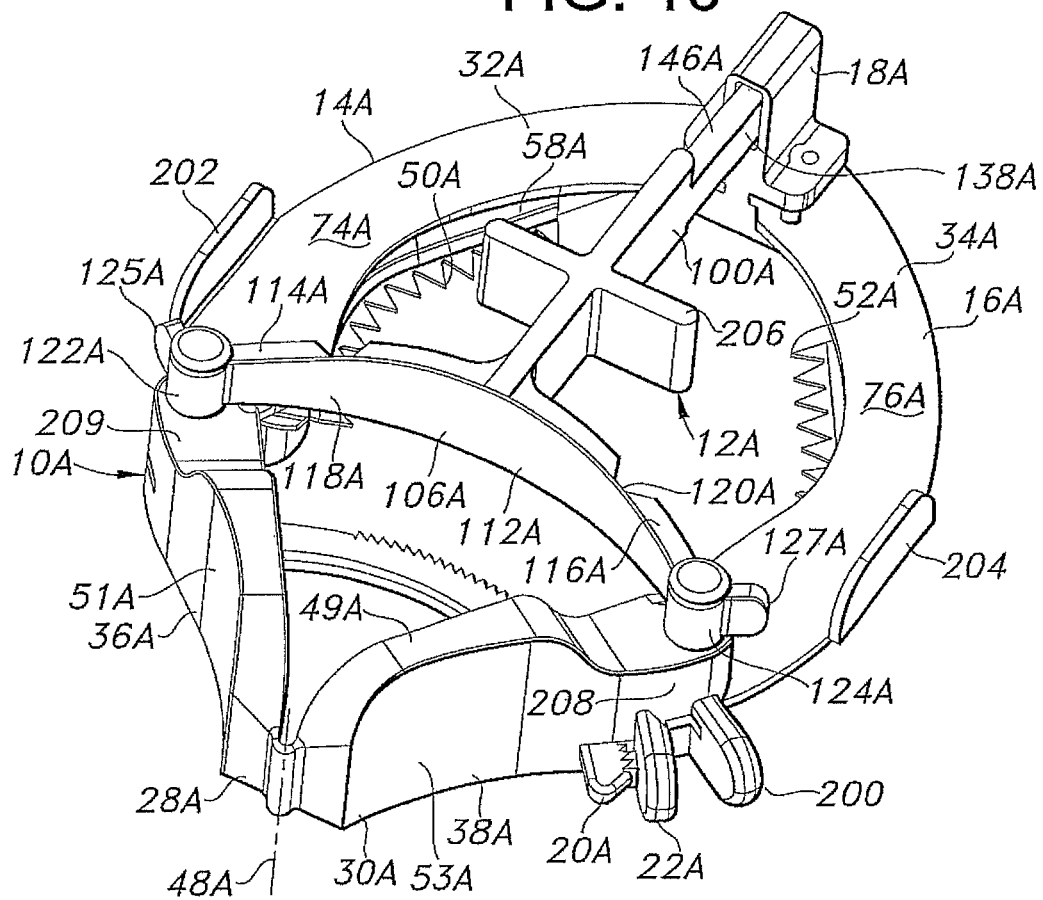
FIG. 17

PATELLA RESECTIONING GUIDE AND ASSEMBLY

CROSS-REFERENCE TO RELATED APPLICATIONS

Priority is claimed to the following U.S. Provisional Patent Application Ser. No. 61/386,097 entitled, "PATELLA RESECTIONING GUIDE AND ASSEMBLY," filed on Sep. 24, 2010 by Maja Kecman, Kyle B. Thomas, Richard A. Hartshorn and Edward H. Goodwin.

TECHNICAL FIELD

The present disclosure relates generally to orthopaedic surgical instruments and more particularly to patella resectioning guides and styluses.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella. To do so, an orthopaedic surgeon may resect the posterior dome side of the patient's natural patella to secure the prosthetic component thereto. In use, the patella component articulates with the patient's natural or prosthetic femur during extension and flexion of the patient's knee.

To facilitate the replacement of the natural joint with the knee prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

In resecting the patella, surgeons frequently perform the resection free-hand. However, free-hand cutting the patella is not as accurate as a guided resection. Moreover, it is important that a sufficient amount of bone stock remain after resection to accept the fixation means for the patella prosthesis and to maintain the integrity of the remaining patella. To ensure that the patella implant is properly positioned and that an appropriate amount of bone remains after resection, a resection guide is needed.

Depending on a number of factors, including the size of the patient, native patellae are of substantially different sizes. Accordingly, if a resection guide is to be used, either the guide must be provided in a plurality of sizes to accommodate variations in patellae size or an adjustable resection guide must be used.

SUMMARY

The present invention provides a patella resection guide that assists the surgeon in performing a guided resection that ensures that the patella implant is properly positioned and that an appropriate amount of bone remains after resection.

In one aspect, the present invention provides a patella resection guide comprising a first arm, a second arm, a connecting member, and a cooperative locking mechanism associated with the first and second arms for releasably locking the arms in a desired position. Each arm has a first end, a second end spaced from the first end, a first portion extending from the first end and a second portion extending from the second end toward the first portion. The first end of the first arm is pivotably connected to the connecting member about a first pivot axis. The first end of the second arm is pivotably connected to the connecting member about a second pivot axis. The first portion of the first arm is pivotably connected to the second portion of the first arm about a third pivot axis. The first portion of the second arm is pivotably connected to the second portion of the second arm about a fourth pivot axis. The first, second, third and fourth pivot axes are parallel to each other. The first portion of the first arm includes a first bone gripping member extending toward the first portion of the second arm and the first portion of the second arm includes a second bone gripping member extending toward the first portion of the first arm. The first bone-gripping member and second bone-gripping member lie in a plane that is substantially perpendicular to the first pivot axis, second pivot axis, third pivot axis and fourth pivot axis and define a space therebetween to receive a patella. The first bone-gripping member and the second bone-gripping member are spaced apart by a distance. The first arm includes a first flat and planar resection guide surface substantially parallel to the plane of the first bone-gripping member. The second arm also includes a second flat and planar resection guide surface substantially parallel to the plane of the first bone-gripping member. The ratchet includes an end fixed to the first arm at a position between the third pivot axis and the second end of the first arm. The second arm includes a ratchet slot positioned between the fourth pivot axis and the second end of the second arm. The ratchet extends from the first arm through the ratchet slot in the second arm. Pivoting the portions of the first and second arms about the first pivot axis, second pivot axis, third pivot axis and fourth pivot axis move the first bone-gripping member and second bone-gripping member toward and away from each other to vary the distance between the first bone-gripping member and the second bone-gripping member. The ratchet locking plate is fixed to the second arm and includes a locking member movable to selectively engage the ratchet to fix the position of the first bone-gripping member with respect to the second bone-gripping member.

The second end of the first arm may be pivotably connected to the second end of the second arm about a fifth pivot axis that is parallel to the first pivot axis, second pivot axis, third pivot axis and fourth pivot axis.

The connections defining all or some of the first pivot axis, second pivot axis, third pivot axis, fourth pivot axis and fifth pivot axis may comprise living hinges.

The second portion of the first arm and second portion of the second arm may include surfaces defining paddles for gripping to close the resection guide. These surfaces defining the paddles may be flat or have curved contours (convex or concave).

The first planar resection guide surface may be co-planar with the second planar resection guide surface.

The first arm, the second arm and connecting member may comprise a unitary polymer base. In such an embodiment, the first planar resection guide surface and second planar guide surface may be parts of elements distinct from and connected to the base. The resection guide may further comprise a first plate and a second plate; the first plate may be mounted to the base and positioned parallel to and spaced from the first planar resection guide surface to define a first guide slot and the second plate may be mounted to the base and positioned parallel to and spaced from the second planar resection guide surface to define a second guide slot. In such an embodiment, the base may extend from the first end to the second end of the first arm and from the first end to the second end of the second arm. In such an embodiment, the first plate may be pivotably connected to the base and the second plate may be pivotably connected to the base.

In any of the above embodiments of this aspect of the invention, the first planar resection guide surface and second planar resection guide surface may comprise channel members extending around part of the base and defining the first and second bone-gripping members.

In any of the above embodiments of this aspect of the invention, the patella resection guide may be part of a patella resection kit further comprising a stylus. In such an embodiment, the connecting member may include an upstanding portion defining a through-slot. In such an embodiment, the second portion of the first arm may include a first upstanding boss having a central longitudinal axis parallel to the first pivot axis, second pivot axis, third pivot axis and fourth pivot axis and the second portion of the second arm may include a second upstanding boss having a central longitudinal axis parallel to the first pivot axis, second pivot axis, third pivot axis and fourth pivot axis. A stylus in such a kit may include an elongate member having parallel first and second edges, a free first end and a second end, a thinner portion at the free first end and a cross-member at the second end of the elongate member. The cross-member may have a first end and a second end, a central portion connected to the second end of the elongate member, a first end portion at the first end and a second end portion at the second end. The first end portion of the cross-member may be pivotably connected to the central portion about a sixth pivot axis, and the second end portion of the cross-member may be pivotably connected to the central portion about a seventh pivot axis. In this embodiment, the first end portion of the cross-member includes a first mounting member and the second end portion of the cross-member includes a second mounting member, the first mounting member and the second mounting member serving to selectively and removably mount the cross-member to the first boss and the second boss of the resection guide. In this embodiment, the stylus is selectively and removably assembled with the resection guide with the thinner portion at the free first end of the elongate member received in the slot in the upstanding portion of the connecting member and the first mounting member and second mounting member engaging the first boss and the second boss. Pivoting the portions of the first arm and second arm of the resection guide about the first pivot axis, second pivot axis, third pivot axis and fourth pivot axis to move the first bone-gripping member and second bone-gripping member toward and away from each other causes the end portions of the styles to pivot with respect to the cross-member and the thinner portion of the elongate member of the stylus to move longitudinally in the through-slot of the upstanding member of the resection guide. When the stylus is assembled with the resection guide the first and second edges of the elongate member of the stylus are parallel to the plane of the first and second resection guide surfaces of the resection guide.

In a particular embodiment of the kit of this aspect of the invention, the stylus and resection guide can be assembled with the stylus being in one of two orientations. In a first orientation, the thinner portion at the free first end of the elongate member is received in the slot in the upstanding portion of the connecting member, the first mounting member and second mounting member engage the first boss and the second boss, and the first edge of the elongate member is nearest the plane of the first and second resection guide surfaces; in this orientation, the distance between the first edge and the plane of the first and second resection guide surfaces is a predetermined first distance. In a second orientation, the thinner portion at the free first end of the elongate member is received in the slot in the upstanding portion of the connecting member, the first mounting member engages the second boss, the second mounting member engages the first boss, and the second edge of the elongate member is nearest the plane of the first and second resection guide surfaces; in this orientation, the distance between the second edge and the plane of the first and second resection guide surfaces is a predetermined second distance. The first predetermined distance is different from the second predetermined distance. The first predetermined distance and the second predetermined distance define the amount of bone to be resected from the patella.

In any of the above embodiments of this aspect of the invention, the cooperative locking mechanism may comprise a ratchet and a ratchet locking plate. In such an embodiment, the ratchet may include a first end fixed to the first arm at a position between the third pivot axis and the second end of the first arm. The ratchet may extend through a ratchet slot in the second arm between the fourth pivot axis and the second end of the second arm. In such an embodiment, the ratchet plate may be fixed to the second arm and may include a locking member movable to selectively engage the ratchet to fix the position of the first bone-gripping member with respect to the second bone-gripping member.

In another aspect of the invention, the invention provides a patella resection assembly comprising a patella resection guide and a stylus. The patella resection guide has a first arm having a first bone-gripping member and a flat and planar saw guide surface, a second arm having a second bone gripping member, and a connecting member connecting the first arm and the second arm. The connecting member has a slot and the first bone gripping member and the second bone gripping member face each other. The stylus is pivotably mounted to the first arm and the second arm and has a free end received in the slot in the connecting member. The first arm and second arm of the patella resection guide are movable to a variety of positions with different distances between the first bone-gripping member and the second bone-gripping member while the stylus is in place connected to the first arm and second arm and with the free end of the stylus within the slot in the connecting member.

In a more particular embodiment of this aspect of the invention, the stylus includes an elongate member that has a first longitudinal edge lying in a plane between the first bone-gripping member and the second bone-gripping member. The plane of the saw guide surface is perpendicular to the plane of the longitudinal edge of the stylus. The distance between the longitudinal edge of the elongate member of the stylus and the plane of the saw guide surface defines the amount of bone to be resected from the patella.

In a more particular embodiment of this aspect of the invention, the stylus includes a second longitudinal edge parallel to the first longitudinal edge. In this embodiment, the stylus may be placed in a first orientation wherein the first longitudinal edge is closest to the plane of the saw guide surface and a second orientation wherein the second longitudinal edge is closest to the plane of the saw guide surface. In the first orientation the distance between the first longitudinal edge and the plane of the saw guide surface is a first predetermined distance and in the second orientation the distance between the second longitudinal edge and the plane of the saw guide surface is a second predetermined distance different from the first predetermined distance.

In a more particular embodiment of this aspect of the invention, the stylus includes a cross-member having a central portion connected to the elongate member and two end portions pivotably connected to the central portion. The end portions includes mounting members for pivotably and removably mounting the stylus to the first arm and second arm of the resection guide.

In a more particular embodiment of this aspect of the invention, the first and second arms of the resection assembly includes a plurality of portions pivotably connected to each other. In a more particular embodiment, a plurality of the pivotable connections comprise living hinges.

In a more particular embodiment of this aspect of the invention, as the first arm and second arm of the patella resection guide are moved between positions with different distances between the first bone-gripping member and the second bone-gripping member, the free end of the stylus moves longitudinally in the slot in the connecting member and the stylus flexes at the connections between the central portion and end portions of the central portion of the stylus.

In any of the above embodiments of this aspect of the invention, the first arm may include a plate spaced from and parallel to the saw guide surface to define a saw guide slot.

In another aspect, the present invention provides a patella resection guide comprising a first arm having a first bone-gripping member and a flat and planar saw guide surface and a second arm having a second bone gripping member. The first arm comprises a plurality of portions linked together into a changeable configuration. The second arm also comprises a plurality of portions linked together into a changeable configuration. The first arm and second arm are movable to a variety of positions with different distances between the first bone-gripping member and the second bone-gripping member; the configurations of the linked portions of the first arm change as the first arm is moved to different positions, and the configurations of the linked portions of the second arm change as the second arm is moved to different positions.

In a particular embodiment of this aspect of the invention, the first arm has a first end and the second arm has a first end connected to the first end of the first arm.

In any of the above embodiments of this aspect of the invention, the patella resection guide further comprises a locking member extending between the first arm and the second arm to lock the first arm and the second arm in desired positions. The locking member may comprise a ratchet and a ratchet locking plate, wherein the ratchet includes an end fixed to the first arm, the second arm includes a ratchet slot, and the ratchet extends from the first arm through the ratchet slot in the second arm.

In any of the above embodiments of this aspect of the invention, the linkages between portions of the first arm comprise living hinges and the linkages between portions of the second arm comprise living hinges.

In any of the above embodiments of this aspect of the invention, the patella resection guide is part of an assembly, the assembly further comprising a stylus pivotably mounted to the first arm and the second arm. In a more particular embodiment, the patella resection guide includes a slot receiving a portion of the stylus; the stylus moves with respect to the patella resection guide as the first arm and second arm are moved between different positions with different distances between the first bone-gripping member and the second bone-gripping member.

In another aspect, the present invention provides a patella resection guide comprising a first arm having a first end, a second end and a first bone-gripping member and a second arm having a first end, a second end and a second bone gripping member. The first arm and second arm are connected by a pivotal connection at the first end of the first arm and the first end of the second arm. The first bone gripping member is between the pivotal connection and the second end of the first arm. The second bone gripping member is between the pivotal connection and the second end of the second arm. The first bone gripping member faces and is spaced from the second bone gripping member. At least part of the first bone gripping member is co-planar with at least part of the second bone gripping member. At least one of the arms includes surfaces defining a resection guide slot lying in a plane parallel to the plane of the first bone gripping member and second bone gripping member. The first arm and second arm are movable to a variety of positions with different distances between the first bone-gripping member and the second bone-gripping member.

In a particular embodiment of this aspect of the invention, the patella resection guide further comprises a connecting member pivotably connected to the first end of the first arm and the first end of the second arm. In this embodiment the connections between the first arm and the connecting member and between the second arm and the connecting member define the pivotal connection between the first end of the first arm and the first end of the second arm.

In another particular embodiment of this aspect of the invention, the patella resection guide further comprises a locking mechanism extending between the first arm and the second arm to lock the first arm and the second arm in desired positions. In this embodiment the first bone-gripping member is positioned between the locking mechanism and the pivotal connection and the second bone-gripping member is between the locking mechanism and the pivotal connection. In a more particular embodiment, the locking mechanism comprises a ratchet and a ratchet locking plate, the ratchet including an end fixed to the first arm and the second arm including a ratchet slot, with the ratchet extending from the first arm through the ratchet slot in the second arm.

In any of the above embodiments of this aspect of the invention, the arms may each include a base portion and planar resection guide surfaces distinct from and connected to the base portions of the arms. In such an embodiment, the resection guide may further comprise first and second plates mounted on the base portions of the arms and positioned parallel to and spaced from the planar resection guide surfaces to define guide slots. In a more particular embodiment, the base portions of the arms comprise a unitary polymer base. These base portions may be connected by a connecting member. The plates may be pivotably connected to the base portions of the arms and the planar resection guide surfaces may comprise channel members extending around parts of the base portions of the arms and define the bone-gripping members. The base portions of the arms may comprise a plurality of portions linked together into configurations that change as the arms are moved to different positions.

In any of the above embodiments of this aspect of the invention, the first arm and the second arm may each comprise a plurality of portions linked together into a changeable configuration. In such an embodiment, the configurations of the linked portions of the arms change as the arms are moved to different positions. In a more particular embodiment, the links between portions of the arms comprise hinges. In a more particular embodiment, these hinges comprise living hinges.

In any of the above embodiments of this aspect of the invention, the patella resection guide may be part of a patella resection kit further comprising a stylus. In such an embodiment, the connecting member may include an upstanding portion defining a through-slot and the arms may include upstanding bosses having spaced, parallel central longitudinal axes. In such an embodiment, the stylus may include an elongate member having parallel first and second edges, a free first end, a second end, a thinner portion at the free first end. Such a stylus may further include a cross-member having a first end, a second end, a central portion connected to the second end of the elongate member, a first end portion at the first end and a second end portion at the second end. In such a stylus, the end portions of the cross-member may include mounting members to selectively and removably mount the cross-member to the upstanding bosses. In this embodiment, the stylus is selectively and removably assembled with the resection guide with the thinner portion at the free first end of the elongate member received in the slot in the upstanding portion of the connecting member and the mounting members engaging the upstanding bosses. When the stylus is assembled with the resection guide the first and second edges of the elongate member of the stylus are parallel to the planes surfaces defining the resection guide slot. In a more particular embodiment, the stylus and resection guide can be assembled with the stylus being in one of two orientations. In a first orientation, the thinner portion at the free first end of the elongate member is received in the slot in the upstanding portion of the connecting member, the mounting members engage the upstanding bosses, the first edge of the elongate member is nearest the planes of the surfaces defining the resection guide slot, and the distance between the first edge and the plane of the nearest surface defining the resection guide slot is a predetermined first distance. In a second orientation, the thinner portion at the free first end of the elongate member is received in the slot in the upstanding portion of the connecting member, the mounting members engaging the upstanding bosses, the second edge of the elongate member is nearest the plane of the surfaces defining the resection guide slot, and the distance between the first edge and the plane of the nearest surface defining the resection guide slot is a predetermined second distance. In this embodiment, the first predetermined distance may be different from the second predetermined distance, and both predetermined distances define different amounts of bone to be resected from the patella.

In any of the embodiments of this aspect of the invention, the stylus may include an additional cross-piece extending out perpendicularly from both sides of the elongate member.

BRIEF DESCRIPTION OF THE DRAWINGS

The detailed description particularly refers to the following figures, in which:

FIG. 15 is an enlarged partial cross-section of the stylus of FIGS. 1-7 and 9-10, taken along line 15-15 of FIG. 10;

FIG. 16 is an enlarged partial cross-section taken along line 16-16 of FIG. 2, showing the end of the stylus received in the connecting member of the resection guide;

FIG. 17 is a perspective view of an assembly of an alternate embodiment of the stylus and resection guide of the present invention, illustrating examples of additional features that may be used with the stylus and resection guide;

DETAILED DESCRIPTION OF THE DRAWINGS

Figure 1:
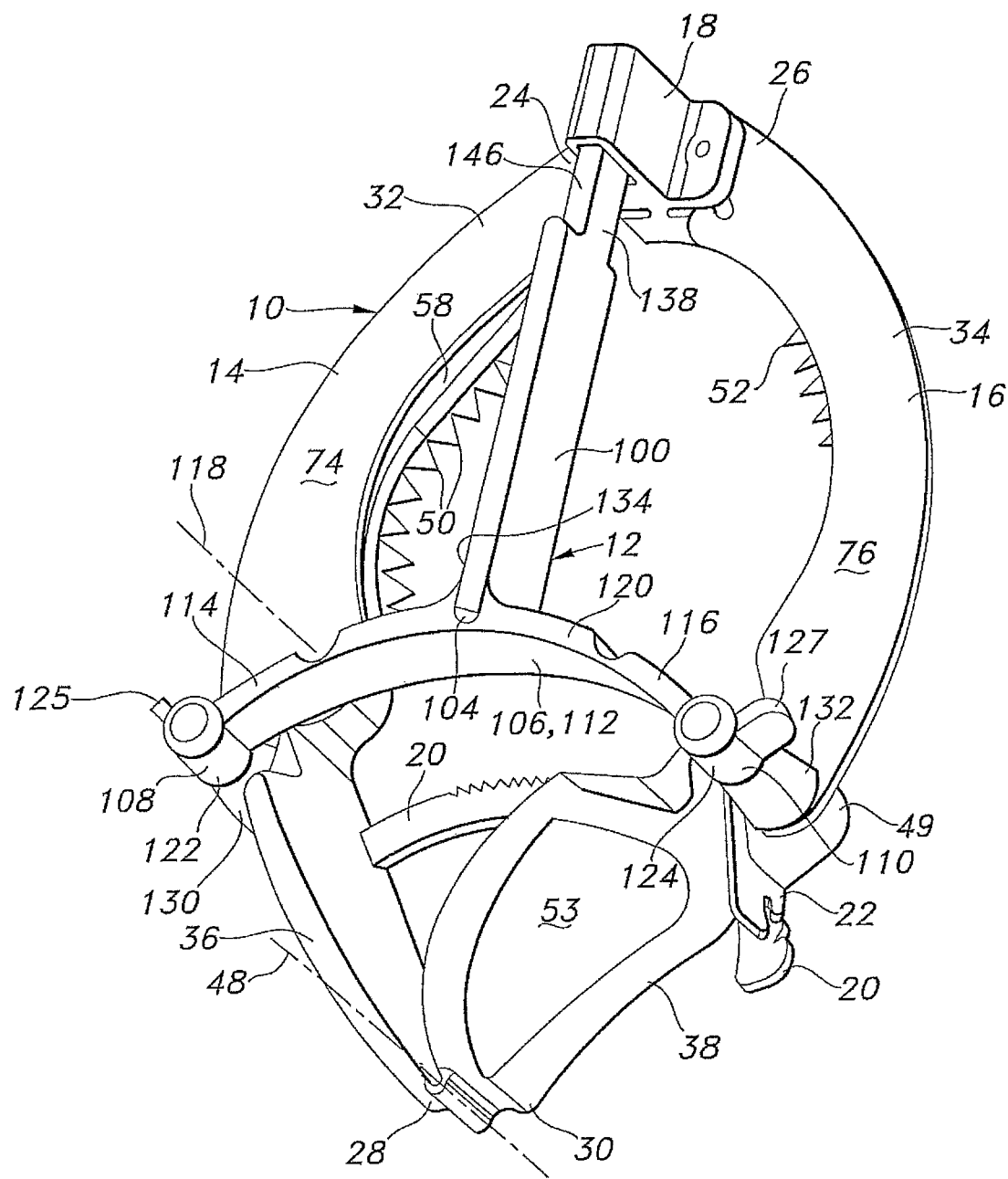
FIG. 1 is a perspective view of one embodiment of an assembly of a patella resection guide and a stylus that illustrate the principles of the present invention, showing the patella resection guide in an expanded position.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, an assembly of a patella resection guide 10 and stylus 12 are illustrated. As discussed in more detail below, the stylus 12 is removably mounted to the resection guide, and is capable of movement with respect to the resection guide 10 as the resection guide 10 is expanded and contracted to mount the assembly to the patient's patella and to remove the assembly from the patient's patella once the desired resection is complete. Typically, the patella resection guide 10 and stylus 12 would be provided in the form of a kit, and assembly would be done intraoperatively, although the components 10, 12 could be provided to the surgeon in a pre-assembled package.

Figure 2:
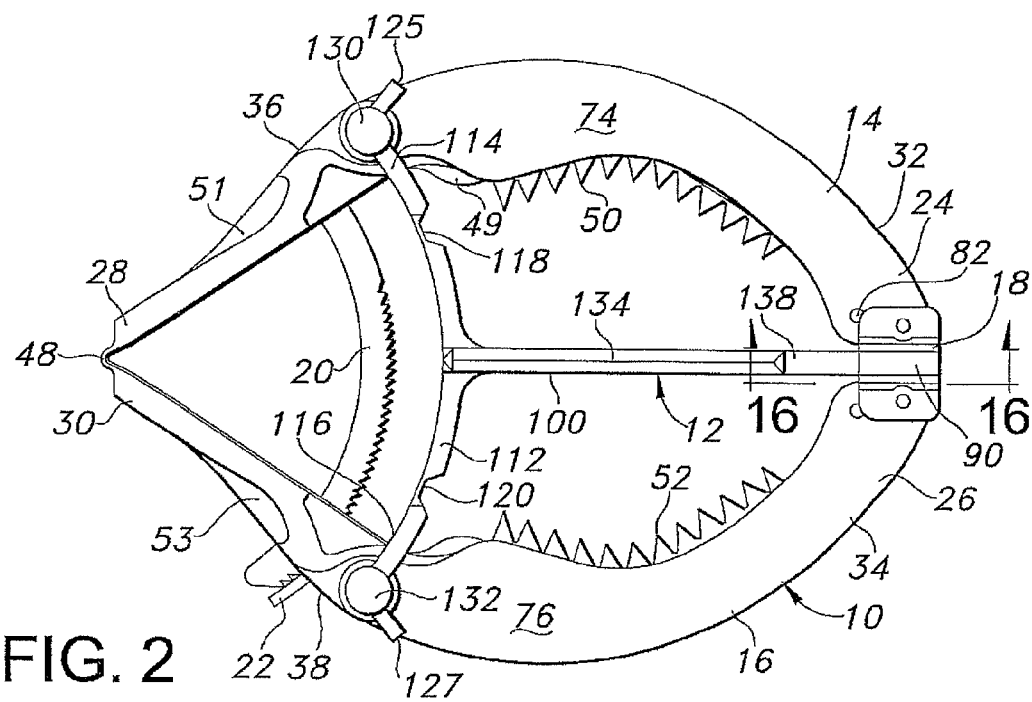
FIG. 2 is a top plan view of the assembly of FIG. 1.
Figure 3:
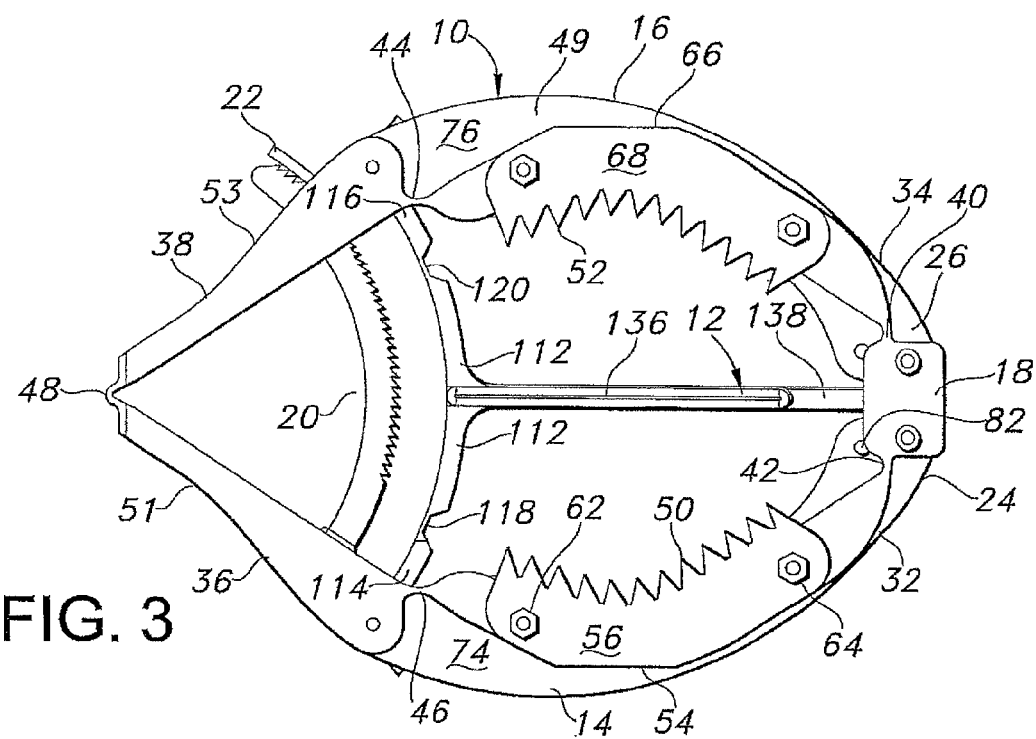
FIG. 3 is bottom plan view of the assembly of FIGS. 1-2.

Turning first to the patella resection guide 10, as shown in FIGS. 1-3 and 7-8 the illustrated patella resection guide 10 comprises a first curved arm 14, a second curved arm 16, a connecting member 18, a curved ratchet 20 and a ratchet locking plate 22. Each arm 14, 16 has a first end 24, 26, a second end 28, 30 spaced from the first end 24, 26, a first portion 32, 34 extending from the first end 24, 26 and a second portion 36, 38 extending from the second end 28, 30 toward the first portion 32, 34. The first end 24 of the first arm 14 is pivotably connected to the connecting member 18 about a first pivot axis 40. The first end 26 of the second arm 16 is pivotably connected to the connecting member 18 about a second pivot axis 42 spaced from the first pivot axis 40. The first portion 32 of the first arm 14 is pivotably connected to the second portion 36 of the first arm 14 about a third pivot axis 44. The first portion 34 of the second arm 16 is pivotably connected to the second portion 38 of the second arm 16 about a fourth pivot axis 46. In the illustrated embodiment, the second end 28 of the first arm 14 is connected to the second end 30 of the second arm 16 about a fifth pivot axis 48. The first pivot axis 40, second pivot axis 42, third pivot axis 44, fourth pivot axis 46 and fifth pivot axis 48 are all parallel to each other, as shown in FIG. 3, where the pivot axes 40, 42, 44, 46, 48 extend outward perpendicularly from the plane of the page.

In the first illustrated embodiment, each of the pivot axes 40, 42, 44, 46, 48 are defined by hinged connections, and more particularly, by living hinges. "Living hinge" as used herein is intended to mean a thin flexible part of an element that joins two rigid parts together, allowing the rigid parts to bend along the line of the hinge.

Figure 11:
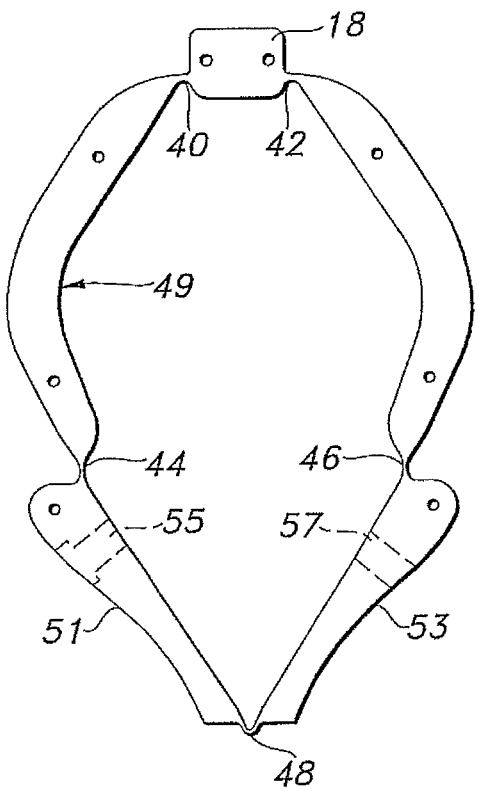
FIG. 11 is a top plan view of the base part of the resection guide shown in FIGS. 1-8.

In the first illustrated embodiment, the patella resection guide 10 comprises an assembly of elements, including a base 49 (illustrated in FIG. 11) and additional components described below. The illustrated base 49 comprises a molded plastic component, and more particularly an injection molded component made as a single, unitary piece of a resin suitable for injection molding and for subsequent sterilization, such as polyethylene or polypropylene, for example. It is anticipated that a number of polymers will be usable to make the base 49, such as polyamide polyphenylsulfone, polyethersulfone, polysulfone, polyketone, and polyarylamide. It will be recognized that any of numerous other plastic materials could be used to form the base 49. The molding operation produces the base 49 with the thinner areas shown at 40, 42, 44, 46 and 48 in FIG. 11. The base 49 is flexible at these thinner areas so that the thinner areas effectively function as living hinges.

The illustrated base 49 also includes two enlarged, concavely contoured paddles 51, 53 adjacent to the fifth pivot axis 48 at the ends 24, 26 of the arms 14, 16 that are sized and shaped to function as grips: the surgeon may squeeze these paddles 51, 53 to contract or close the resection guide 10 against the patella. It should be understood that the surfaces defining the paddles may have other shapes, such as a convex contour or a flat contour. In addition, the second portions 36, 38 of the arms 14, 16 include curved slots 55, 57 (shown in phantom in FIG. 11) to receive portions of the curved ratchet 20. One of the slots 55 and one end of the ratchet 20 have complementary end shapes so that one end of the ratchet 20 can be fixed to one arm 14 while the other end of the ratchet is free to move through the slot 57 in the other arm 16.

Figure 7:
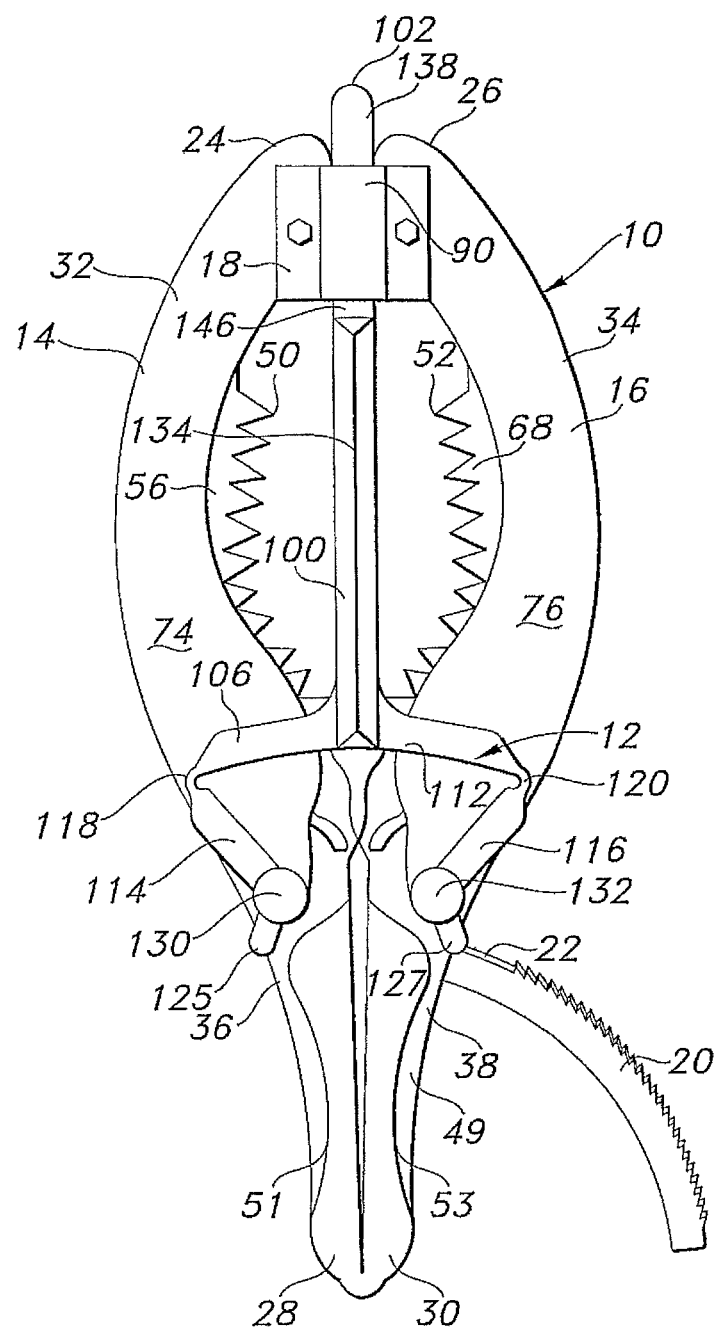
FIG. 7 is a top plan view similar to FIG. 2, showing the assembly in a contracted position.
Figure 8:
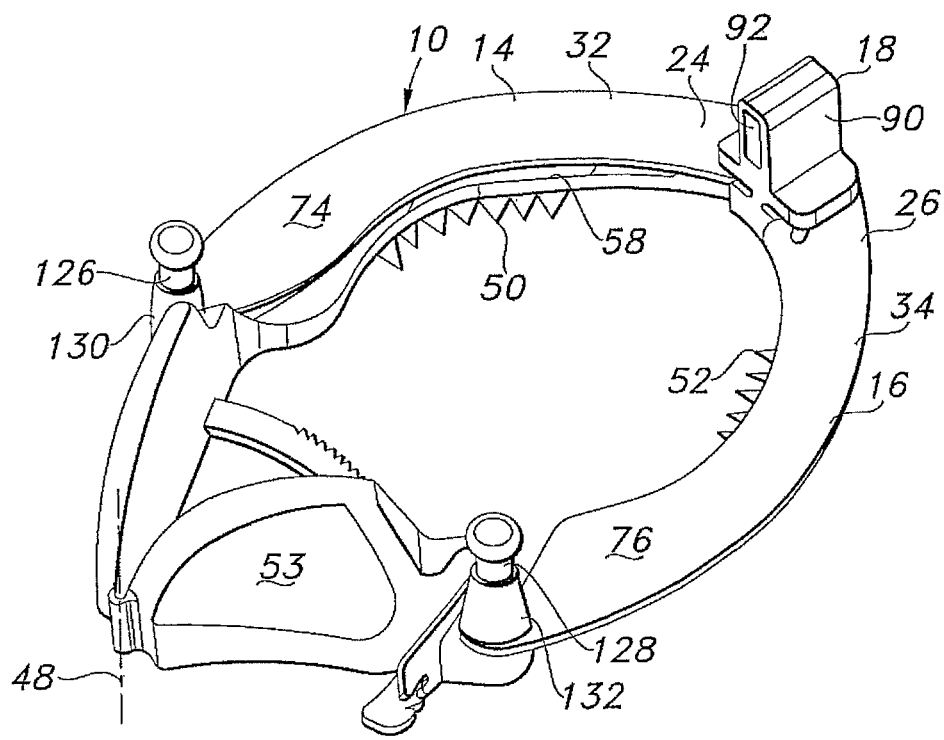
FIG. 8 is a perspective view of the patella resection guide of FIGS. 1-7, showing the resection guide without the stylus.

It should be understood that the illustrated ratchet 20 and ratchet locking plate 22 represent one example of a releasable locking mechanism that may be used to lock the arms 14, 16 in a particular configuration, such as the open configuration of FIGS. 1-3, 8 and 17-19 and the closed configuration of FIG. 7. Other locking mechanisms may be used: for example, clutch plates used in "quick clamps" may be used.

Two of the additional components assembled with the base 49 to form the patella resection guide 10 are a set of bone-gripping members. As shown in FIGS. 2-3, the first portion 32 of the first arm 14 has a first bone-gripping member 50 extending toward the first portion 34 of the second arm 16 and the first portion 34 of the second arm 16 has a second bone-gripping member 52 extending toward the first portion 32 of the first arm 14. The bone-gripping members 50, 52 in the illustrated embodiment comprise a plurality of teeth with their points facing each other. A space is defined between the points of the teeth in which the patella is received and gripped by the teeth about its periphery, as described in more detail below. All of the teeth of the bone-gripping members 50, 52 lie in a plane that is perpendicular to the pivot axes 40, 42, 44, 46, 48 of the resection guide 10. The teeth are oriented so that when the patella is received between and engaged by the teeth, a plurality of points on the patella are engaged (such as three spaced points) so that the patella is held with no relative movement between the patella and the patella resection guide. In the illustrated embodiment the teeth of the bone-gripping members 50, 52 are integral parts of planar plates or sheets that are parts of channel members.

Figure 5:
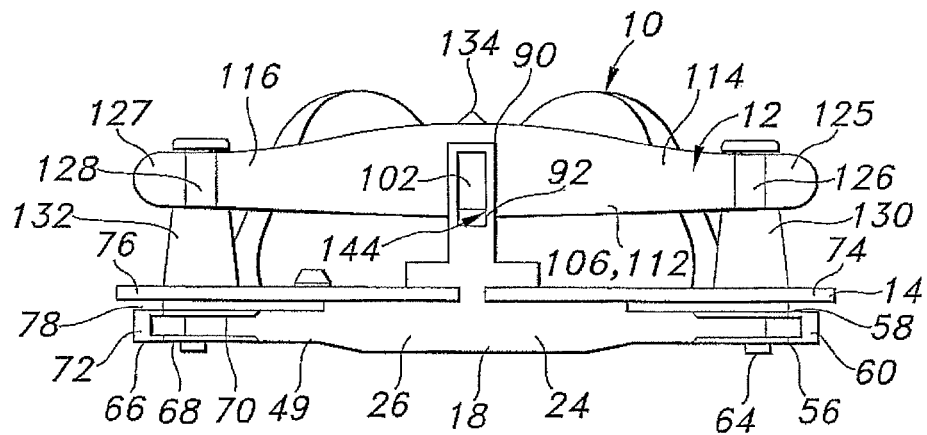
FIG. 5 is a an end elevation of the assembly of FIGS. 1-4 taken along line 5-5 of FIG. 4.
Figure 6:
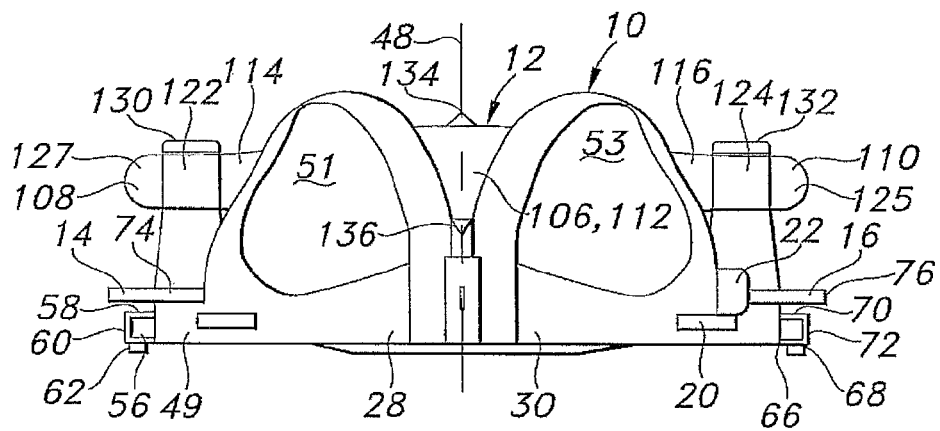
FIG. 6 is an end elevation view of the assembly of FIGS. 1-5, taken along line 6-6 of FIG. 4.
Figure 12:
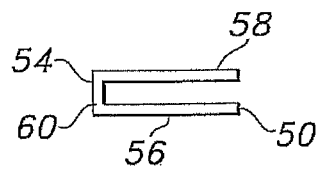
FIG. 12 is an end view of one of the metal plates defining the bone-gripping members of the resection guide of FIGS. 1-8.
Figure 13:
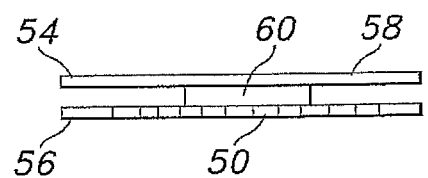
FIG. 13 is a front elevation of the metal plate of FIG. 12.

An example of such a channel member is shown at 54 in FIGS. 12-13, where the plate or sheet that is shaped to define the bone-gripping teeth 50 is labeled 56. The channel member 54 is C-shaped or U-shaped in end view and includes another planar plate or sheet 58 that overlies and is substantially parallel to the plate 56. The two plates or sheets 56, 58 are connected by a perpendicular plate 60. A reduced-thickness portion of the base 49 is received in the space between the plates or sheets 56, 58, and the channel member is fixed to this portion of the base 49 through bolts, rivets or the like (shown in FIG. 3 at 62 and 64) extending through aligned holes formed in the plates or sheets 56, 58. The bone-gripping member 52 of the second arm 16 is essentially the mirror image of the structure described above for the first arm 14, and the above description applies to the channel member of the second arm 16 as well; in FIGS. 3 and 5-6, the channel member of the second arm 16 is labeled 66, the parallel plates are labeled 68, 70 and the perpendicular connecting plate is labeled 72.

In the illustrated embodiment, the top surfaces of the plates 58, 70 of the channel members 54, 66 define co-planar first and second resection guide surfaces. The surgeon may rest a saw blade on these surfaces of these plates 58, 70 to resect the posterior dome of the patella.

Two additional plates are assembled with the base 49 to define the first and second arms 14, 16 of the illustrated patella resection guide 10. These additional top plates are labeled 74 and 76 in FIGS. 1-8 and are positioned above and parallel to the first and second resection guide surfaces defined by the top surfaces of the plates 58, 70 of the channel members 54, 66. The upper plates 74, 76 define parallel upper and lower planar surfaces that are parallel to and spaced the plane of the top surfaces of the plates 58, 70 to define co-planar saw guide slots, sized and shaped so that a saw blade may pass through the guide slots. One of the guide slots is shown at 78 in FIGS. 4 and 5. Both the upper and lower surfaces of the upper plates 74, 76 define planar guide surfaces for the saw blade: instead of using the guide slot such as slot 78, the surgeon may rest the saw blade against the top surface of one of the plates 74, 76 to guide the saw blade during resection of the patella.

The channel members 54, 66, including the teeth of the opposed bone-gripping members 50, 52, and the upper plates 74, 76 may be cut from a sheet of metal, by laser cutting, stamping, drilling, or otherwise cutting the sheet. The channel members 54, 66 may then be formed from the cut sheets. The metal may comprise, for example, stainless steel or other metal suitable for orthopaedic instruments. It should be understood that other materials may be used as well, and the present invention is not limited to the use of stainless steel unless expressly called for in the claims. Generally, any material that has sufficient stiffness and that will not be damaged by the action of the saw blade acting against it is acceptable.

Figure 14:
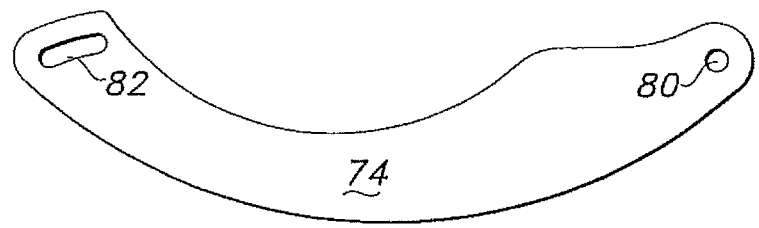
FIG. 14 is a top plan view of one of the top metal plates of the resection guide of FIGS. 1-8.
Figure 18:
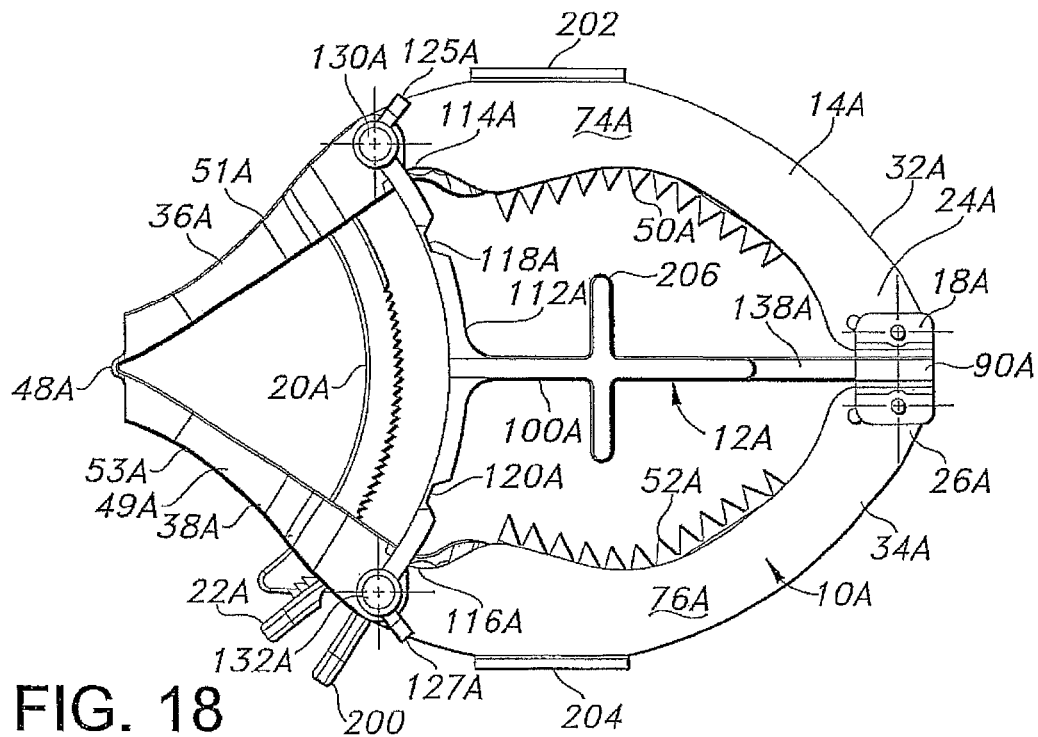
FIG. 18 is a top plan view of the assembly of FIG. 17.
Figure 19:
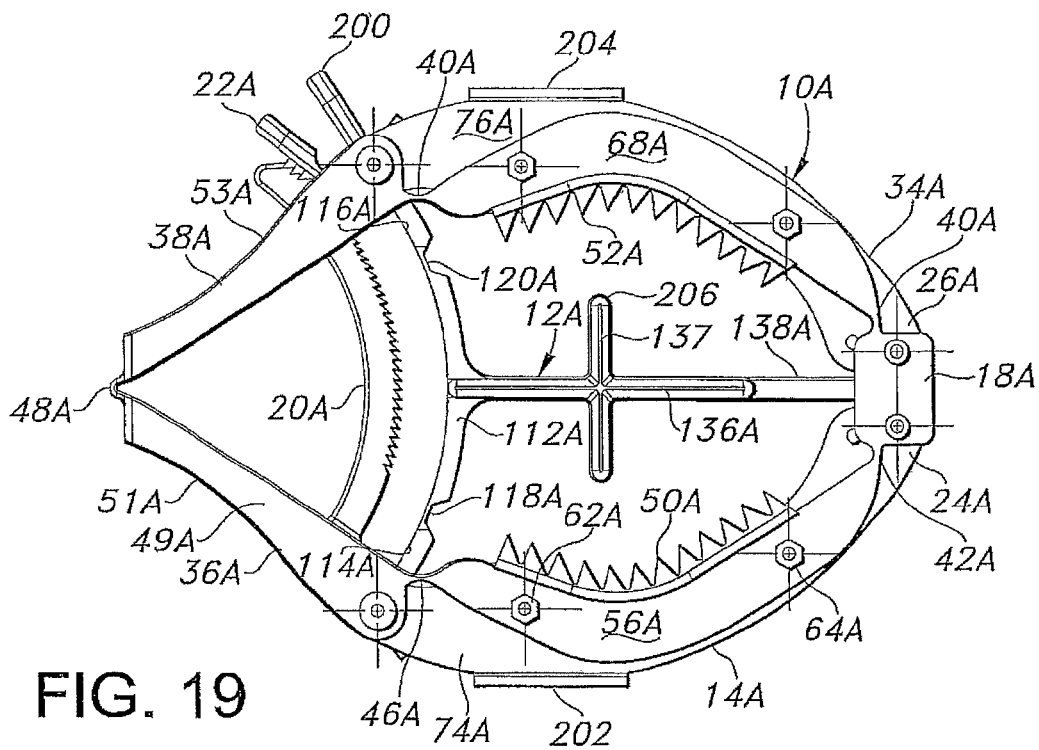
FIG. 19 is a bottom plan view of the assembly of FIGS. 17-18.
Figure 20:
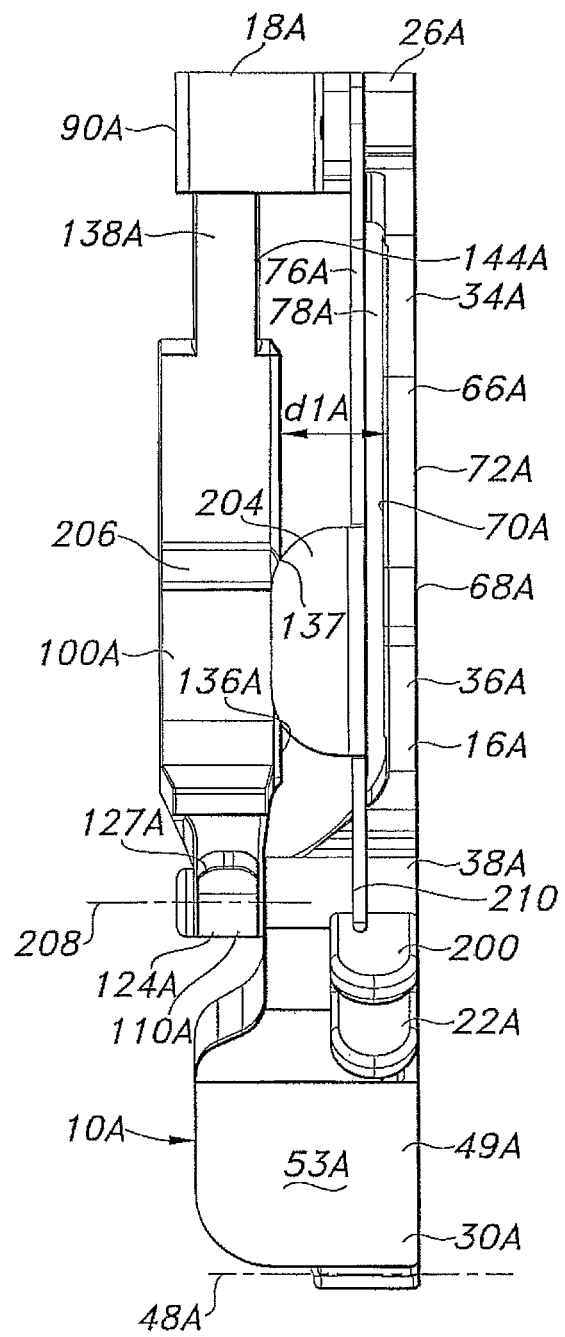
FIG. 20 is a side elevation of the assembly of FIGS. 17-19.

FIG. 14 illustrates an example of one of the upper plates 74 of the first illustrated embodiment. As there illustrated, the upper plate 74 includes a through hole 80 at one end and a slot 82 at its opposite end. The other plate 76 is the mirror image of the plate illustrated in FIG. 14.

The plates 74, 76 are mounted to the base 49 through connections that allow both ends of the plates to pivot with respect to the base. Pins or the like may be used. The ends of the plates 74, 76 that are adjacent to the slots 82 are received within slots in the connecting member 18 of the base 49 through bolts that extend through the slots 82 and nuts that allow these ends of the plates 74, 76 to pivot and slide with respect to the base as the resection guide is expanded and contracted against the patella. The through holes 80 of the plates 74, 76 are mounted on spindles or pins that extend upwardly from the base 49. The plates 74, 76 are sized and shaped so that the connections through the slots 82 are at the first ends 24, 26 of the arms 14, 16 and the connections through the through holes 80 are at the second portions 36, 38 of the arms 14, 16. Thus, as shown in FIG. 3, the plates 74, 76 span the first, second, third and fourth hinges and pivot axes 40, 42, 44, 46. With these connections, the relative positions of the plates 74, 76 and the channel members (e.g. 66) change as the resection guide is expanded and contracted, although the plates 74, 76 and the sheets 58, 70 remain parallel with a constant distance between the parallel surfaces as the resection guide is expanded and contracted.

Referring back to the connecting member 18 of the resection guide 10, the connecting member 18 includes an upstanding portion 90 defining a through slot 92 (see FIG. 8) aligned along a central longitudinal plane through the resection guide 10. As shown in FIG. 16, the connecting member 18 includes a support surface 94 within the slot 92 that supports a portion of the stylus 12.

Figure 9:
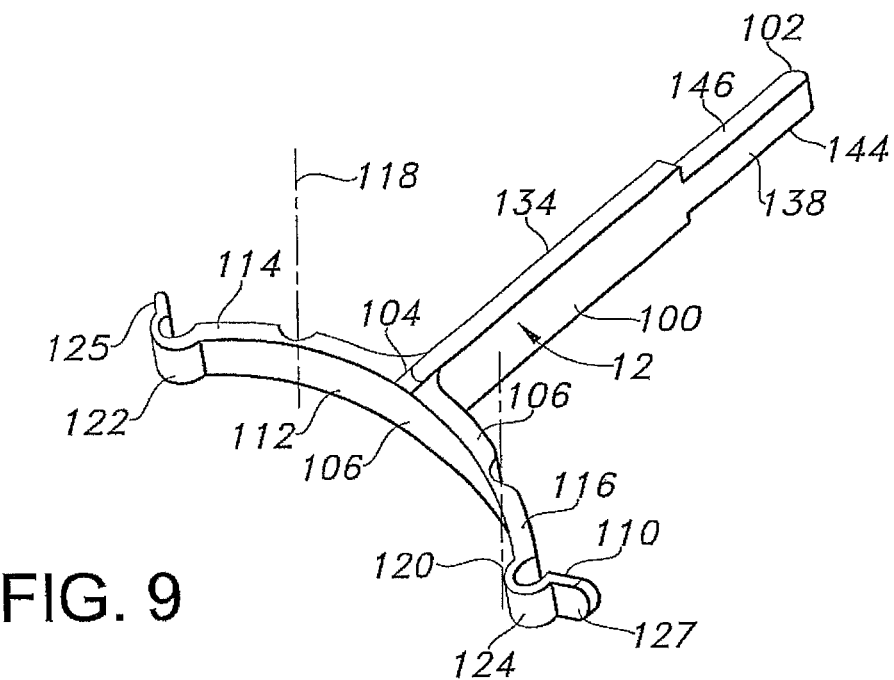
FIG. 9 is a perspective view of the stylus of FIGS. 1-7, showing the stylus without the resection guide.

As shown in FIG. 9, the stylus 12 includes an elongate member 100 having a free end 102 and a second end 104. A cross-member 106 is integral with and extends from the elongate member 100. The cross-member 106 has a first end 108, a second end 110, and a central portion 112 integral with the second end 104 of the elongate member 100. A first end portion 114 is at the first end 108 and a second end portion 116 is at the second end 110. The first end portion 114 is pivotably connected to the central portion 112 about a sixth pivot axis 118 and the second end portion 116 is pivotably connected to the central portion 112 about a seventh pivot axis 120.

The first end portion 114 of the stylus 12 includes a first mounting member 122 and the second end portion 116 of the stylus 12 includes a second mounting member 124. The mounting members 122, 124 in the illustrated embodiment comprise semi-cylindrical concave surfaces formed in thinner, more flexible portions of the stylus, and end tabs 125, 127 extending outward for grasping. The mounting members 122, 124 are sized and shaped to be snap fit about cylindrical portions 126, 128 (see FIG. 8) of upstanding bosses 130, 132 on the resection guide 10.

Figure 10:
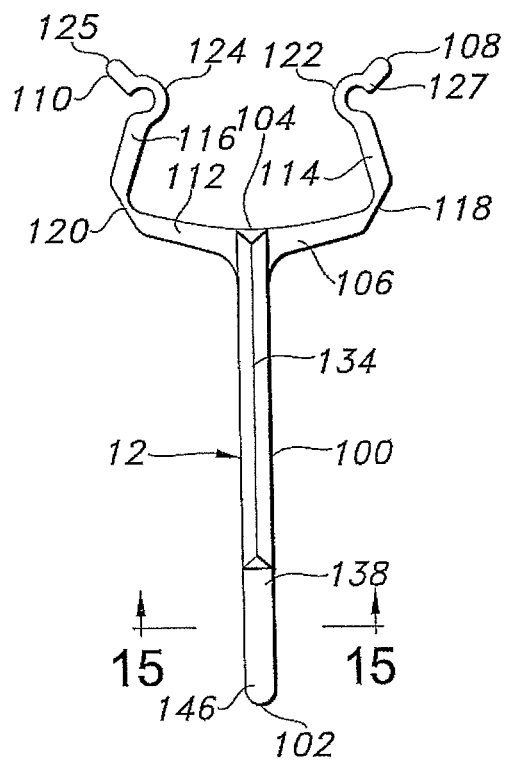
FIG. 10 is a top plan view of the stylus of FIG. 9, showing the end portions of the cross-member of the stylus pivoted to a different position than the position shown in FIG. 9.

In the first illustrated embodiment of the stylus 12, each of the pivot axes 118, 120 are defined by hinged connections, and more particularly, by living hinges, similar to the living hinges described above for the resection guide 10. Like the base 49 of the resection guide 10, the stylus 12 in the illustrated embodiment comprises a molded plastic component, and more particularly an injection molded component made as a single, unitary piece of a resin suitable for injection molding and for subsequent sterilization, such as polyethylene or polypropylene, for example, although other polymers such as polyamide polyphenylsulfone, polyethersulfone, polysulfone, polyketone, and polyarylamide are expected to be usable. The molding operation produces the stylus 12 with the thinner areas shown at 118 and 120, along with the thinner more flexible mounting members 122, 124 to allow the mounting members to be snap fit around the cylindrical portion 126, 128 of the bosses 130, 132 to removably mount the stylus 12 to the resection guide 10. The living hinges at axes 118, 120 allow the first and second end portions 114, 116 to bend between the positions illustrated in FIG. 9 and FIG. 10.

Figure 4:
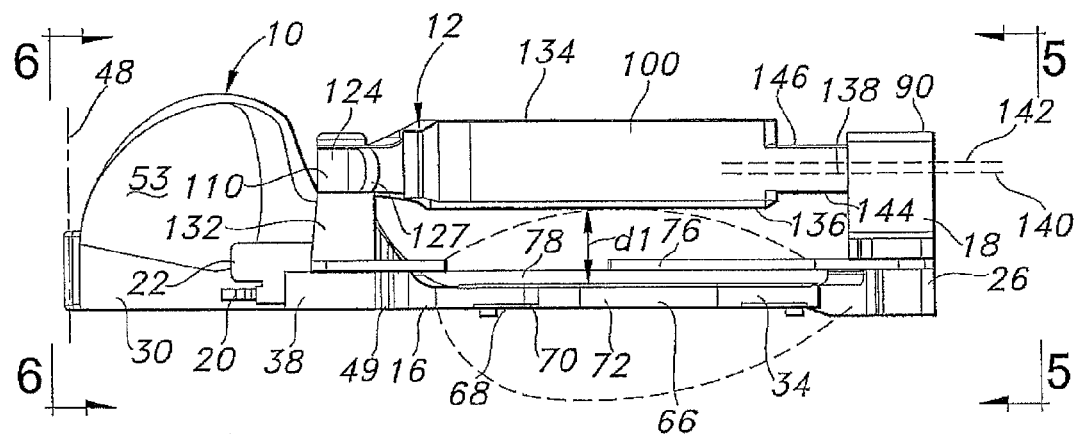
FIG. 4 is a side elevation of the assembly of FIGS. 1-3, with a patella shown in phantom.

The elongate member 100 of the stylus 12 has top and bottom surfaces that taper along a portion of their lengths to longitudinal edges 134, 136. When the stylus 12 is mounted to the resection guide as shown in FIG. 4, the longitudinal edges 134, 136 lie in planes that are parallel to and spaced at predetermined distances from the planes of the plates 58, 70, 74, 76 and guide slot 78.

Figure 4A:
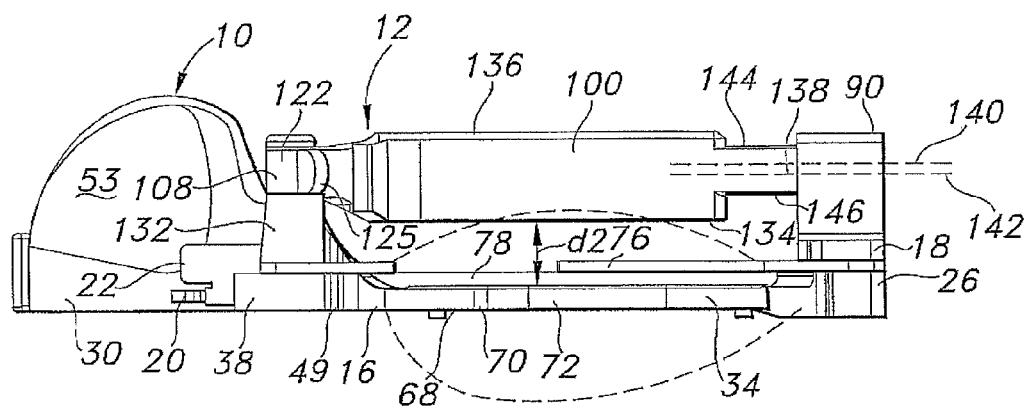
FIG. 4A is a side elevation similar to FIG. 4, but with the stylus flipped 180 degrees and with a patella shown in phantom.

In the illustrated embodiment, the elongate member 100 of the stylus 12 has a thinner portion 138 at the free end 102 extending toward the main body of the elongate member 100. As can be seen in FIGS. 4 and 15, the central longitudinal axis 140 of the thinner portion 138 is vertically offset from the central longitudinal axis 142 of the main body of the elongate member 100. Thus, as shown in FIG. 4, when one longitudinal edge 144 of the thinner portion 138 rests on the support surface 94 within the slot 92 of the upstanding portion 90 of the connecting member 18 and the first flexible mounting member 122 engages the first boss 130 and the second flexible mounting member 124 engages the second boss 132, the nearest edge 136 of the main body of the elongate member 100 lies in a plane that is spaced a first predetermined vertical distance d1 from the plane of the resection guide surfaces defined by the plates 58, 70 of the resection guide slot 78. The stylus 12 can be flipped 180 degrees to the position shown in FIG. 4A. As shown in FIG. 4A, when the opposite longitudinal edge 146 of the thinner portion rests on the support surface 94 within the slot 92 of the upstanding portion 90 of the connecting member 18 and the first flexible mounting member 122 engages the second boss 132 and the second flexible mounting member 124 engages the first boss 130, the nearest edge 134 of the main body of the elongate member 100 lies in a plane that is spaced a second predetermined vertical distance d2 from the plane of the resection guide surfaces defined by the plates 58, 70 of the resection guide slot 78. As discussed in more detail below, the first and second predetermined vertical distances correspond with the depth of resection of the patella, and may be, for example, 11 mm and 8.5 mm, or some other desired distances. Indicia of the resection depth can be molded into or marked on the stylus if desired; for example, the stylus could be marked with a reference to 11 mm and a reference to 8.5 mm and with arrows pointing from the numbers to the appropriate edge. If the surgeon chooses to use the top surfaces of the plates 74, 76 as the guide surfaces for the patella resection, additional patella resection levels are available to the surgeon.

An alternative embodiment is illustrated in FIGS. 17-20. This embodiment is similar to that shown in the first embodiment. Like parts have been labeled in the figures with like numbers, followed by the letter "A". The above description of similarly labeled parts applies to the second embodiment as well as the first described embodiment.

Some of the additional features provided by the embodiment of FIGS. 17-20 relate to ergonomics. For example, an integral flange 200 is provided adjacent to the ratchet locking plate 22A to make it easier for the surgeon to unlock the ratchet 20A when desired. In the embodiment of FIGS. 17-20, opposing finger grips 202, 204 are also provided on the outermost edges of the plates 74, 76. These finger grips 202, 204 provide convenient contact areas for the surgeon to use when expanding and contracting the resection guide. The stylus 12A of the embodiment of FIGS. 17-20 includes an additional cross-piece 206 extending out perpendicularly from both sides of the elongate member 100A for added stability. The cross-piece 206 includes a transverse edge 137 intersecting and co-planar with the longitudinal edge 136A.

One feature of the embodiment of FIGS. 17-20 that differs from the first illustrated embodiment is that in the embodiment of FIGS. 17-20, the bosses are not discreet components assembled with the base 49 and plates 74, 76, like the bosses 130, 132. Instead, integral portions 208, 209 of the second portion 36A, 38A of each arm have slots (shown at 210 in FIG. 20) that receive the ends of the top plates 74A, 76A and define cylindrical bosses like those shown at 126 and 128 to which the stylus 12A may be mounted. A spindle or post (not shown) extends through the bosses of the integral portions 208, 209 for rotatably or pivotably mounting the plates 74A, 76A to the second portions 36A, 38A of the base 49A. In addition, the paddles 51A, 53A are shaped to have a lower profile in the embodiment of FIGS. 17-20.

Another feature of the embodiment of FIGS. 17-20 that differs from the first illustrated embodiment is that in the embodiment of FIGS. 17-20, the ratchet 20A is injection molded as an integral part of the second portion 36A of the first arm 14A rather than as a separate element assembled with the molded base 49 as in the first illustrated embodiment.

To use the patella resection guide 10, 10A and stylus 12, 12A of the present invention, the surgeon would make a standard incision and then partially or fully evert the patient's patella to expose the posterior side of the patella. If not pre-assembled, the surgeon would determine the preferred level of resection (for example, 8.5 mm or 11 mm) and the surgeon or operating room staff would then flip the stylus 12, 12A to the appropriate orientation (that is with either edge 144 or edge 146 facing down) for the preferred level of resection, then assemble the resection guide 10, 10A and the stylus 12, 12A by inserting the end 102, 102A of the stylus 12, 12A in the slot 92 of the upstanding member 90 and snapping the mounting members 122, 124, 122A, 124A onto the cylindrical portions 126, 128 of the bosses 130, 132 or bosses 208, 209 of the resection guide 10A.

With the resection guide 10, 10A in the expanded position (such as shown in FIGS. 1 and 17), the surgeon places the assembly such that the arms 14, 14A, 16, 16A are near opposed peripheral edges (either medial and lateral edges or superior and inferior edges) of the patella. The lower longitudinal edge 134 (or 136, 136A if the stylus is oriented with this edge facing downward toward the plates 74, 74A, 76, 76A) is placed against a surface of the patella, such as the most posterior surface of the patella. If the stylus has a cross-piece such as cross-piece 206 in the embodiment of FIGS. 17-20, the additional transverse edge 137 provides additional stability for placement of the stylus on the posterior patella surface. Thus, the saw guide slots 78, 78A are positioned at a known, fixed distance from the desired surface of the patella to set the resection level with reference to this patella surface.

The surgeon may then close or contract the patella resection guide 10, 10A about the patella until the gripping members or teeth 50, 50A, 52, 52A contact and grip the periphery of the patella. In the first embodiment, the surgeon may close or contract the patella resection guide 10 by squeezing the paddles 51, 53. In the second embodiment, the surgeon may close or contract the patella resection guide 10, 10A about the patella by squeezing the finger grips 202, 204 or the paddles 51A, 53A. As the surgeon closes or contracts the resection guide 10, 10A, the arms 14, 14A, 16, 16A pivot on their axes 40, 40A, 42, 42A, 44, 44A, 46, 46A, 48, 48A and the plates 74, 74A, 76, 76A pivot and slide with respect to the base 49, 49A. Simultaneously, the stylus 12, 12A pivots about the cylindrical portions (elements 126, 128 in the first embodiment) of the bosses 130, 132 of the resection guide 10 (or bosses of the integral portions 208, 209 of the resection guide 10A) and about the pivot axes 118, 118A, 120, 120A, and the thinner portion 138, 138A of the stylus translates on the surface 94 in the slot 92.

As the surgeon closes or contracts the resection guide 10, 10A, the second portions 36, 36A, 38, 38A of the arms 14, 14A 16, 16A move closer together and the ratchet 20, 20A moves with respect to the second portion 38, 38A of arms 16, 16A. As the ratchet 20, 20A moves, its teeth are engaged by the locking plate 22, 22A. When the gripping members 50, 50A, 52, 52A squeeze the patella periphery between them, the patella is firmly gripped and the locking plate 22, 22A locks the ratchet 20, 20A and the arms 14, 14A, 16, 16A in this position. Thus, the resection guide 10, 10A is fixed in a desired position with respect to the patient's patella, with the resection guide slots 78, 78A positioned so that the predetermined desired level of resection is set. The surgeon may then place a saw blade through one of the guide slots 78, 78A or on the surface of one of the plates 74, 74A, 76, 76A and perform the resection. Once the resection is complete, the surgeon may disengage the locking plate 22, 22A from the ratchet 20, 20A, expand the resection guide and remove the resection guide.

It should be understood that the surgeon may optionally remove the stylus 12, 12A from the resection guide 10, 10A before performing the resection. To remove the stylus, the surgeon may easily press on the tabs 125, 125A, 127, 127A to release the mounting members 122, 122A, 124, 124A and slide the end 102, 102A of the stylus 12, 12A out of the slot 92, 92A.

It will be appreciated by comparing FIGS. 1 and 7 that the distance between the bone-gripping members 50, 50A, 52, 52A varies substantially between the fully open or expanded position of FIG. 1 and the fully closed or contracted position of FIG. 7. The resection guide can be locked in substantially any position between those shown in FIGS. 1 and 7. Thus, a single resection guide 10, 10A and stylus 12, 12A can be used to resect patellae of a large variety of sizes.

It should also be appreciated that features of the resection guide and stylus may be varied from those described above. For example, the illustrated embodiments use living hinges to define the pivot axes 40, 40A, 42, 42A, 44, 44A, 46, 46A, 48, 48A, 118, 118A, 120, 120A; such hinges allow for parts of the resection guide and stylus to be injection molded. Such living hinges are well-suited for resection guides and styluses that are intended for a limited number of uses, and are particularly well-suited for guides and styluses that are intended for a single use. For guides and styluses intended to multiple uses, more robust mechanical hinges may be more appropriate.

Thus, the patella resection guide 10, 10A of the present invention may be clamped onto patellae of various sizes, with the stylus 12, 12A in place. Regardless of the size of the patella, an accurate resection may be performed. In addition, substantial parts of the assembly may be made relatively inexpensively (by injection molding of polymers, for example). The patella resection guide 10, 10A and stylus 12, 12A are thus suitable for economical use as single use instruments.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

We claim:

1. A patella resection guide comprising a first arm, a second arm, a connecting member, a cooperative locking mechanism associated with the first arm and the second arm for releasably locking the first and second arms in a desired position, wherein:
    each arm has a first end and a second end spaced from the first end;
    each arm has a first portion extending from the first end and a second portion extending from the second end toward the first portion;
    the first end of the first arm is pivotably connected to the connecting member about a first pivot axis;
    the first end of the second arm is pivotably connected to the connecting member about a second pivot axis;
    the first portion of the first arm is pivotably connected to the second portion of the first arm about a third pivot axis;
    the first portion of the second arm is pivotably connected to the second portion of the second arm about a fourth pivot axis;
    the first pivot axis, second pivot axis, third pivot axis and fourth pivot axis are parallel to each other;
    the first portion of the first arm includes a first bone gripping member extending toward the first portion of the second arm;
    the first portion of the second arm includes a second bone gripping member extending toward the first portion of the first arm;
    the first bone-gripping member and second bone-gripping member lie in a plane that is substantially perpendicular to the first pivot axis, second pivot axis, third pivot axis and fourth pivot axis and define a space therebetween to receive a patella;
    the first bone-gripping member and the second bone-gripping member are spaced apart by a distance;
    the first arm includes a first planar resection guide surface substantially parallel to the plane of the first bone-gripping member;
    the second arm includes a second planar resection guide surface substantially parallel to the plane of the first bone-gripping member;
    pivoting the portions of the first and second arms about the first pivot axis, second pivot axis, third pivot axis and fourth pivot axis move the first bone-gripping member and second bone-gripping member toward and away from each other to vary the distance between the first bone-gripping member and the second bone-gripping member; and
    the connections defining the first pivot axis, second pivot axis, third pivot axis and fourth pivot axis comprising living hinges.

2. The patella resection guide of claim 1 wherein the second portion of the first arm and second portion of the second arm include surfaces defining paddles.

3. The patella resection guide of claim 1 wherein the first planar resection guide surface is co-planar with the second planar resection guide surface.

4. The patella resection guide of claim 1 wherein the cooperative locking mechanism comprises a ratchet and a ratchet locking plate, the ratchet including a first end fixed to the first arm at a position between the third pivot axis and the second end of the first arm, the ratchet extending through a ratchet slot in the second arm between the fourth pivot axis and the second end of the second arm, the ratchet locking plate being fixed to the second arm and including a locking member movable to selectively engage the ratchet to fix the position of the first bone-gripping member with respect to the second bone-gripping member.

5. The patella resection guide of claim 1 further comprising a stylus, wherein:
    the connecting member includes an upstanding portion defining a through-slot;
    the second portion of the first arm includes a first upstanding boss having a central longitudinal axis parallel to the first pivot axis, second pivot axis, third pivot axis and fourth pivot axis;
    the second portion of the second arm includes a second upstanding boss having a central longitudinal axis parallel to the first pivot axis, second pivot axis, third pivot axis and fourth pivot axis;
    the stylus includes:
        an elongate member having parallel first and second edges, a free first end and a second end and a thinner portion at the free first end; and
        a cross-member at the second end of the elongate member, the cross-member having a first end and a second end, a central portion connected to the second end of the elongate member, a first end portion at the first end and a second end portion at the second end, the first end portion of the cross-member being pivotably connected to the central portion about a sixth pivot axis, and the second end portion of the cross-member being pivotably connected to the central portion about a seventh pivot axis, the first end portion of the cross-member including a first mounting member and the second end portion of the cross-member including a second mounting member, the first mounting member and the second mounting member serving to selectively and removably mount the cross-member to the first boss and the second boss of the resection guide;
    the stylus is selectively and removably assembled with the resection guide with the thinner portion at the free first end of the elongate member received in the slot in the upstanding portion of the connecting member and the first mounting member and second mounting member engaging the first boss and the second boss;
    pivoting the portions of the first arm and second arm of the resection guide about the first pivot axis, second pivot axis, third pivot axis and fourth pivot axis to move the first bone-gripping member and second bone-gripping member toward and away from each other causes the end portions of the styles to pivot with respect to the cross-member and the thinner portion of the elongate member of the stylus to move longitudinally in the through-slot of the upstanding member of the resection guide;

and when the stylus is assembled with the resection guide the first and second edges of the elongate member of the stylus are parallel to the plane of the first and second resection guide surfaces of the resection guide.

6. The patella resection guide of claim 5 wherein the stylus and resection guide can be assembled with the stylus being in one of two orientations, including:

a first orientation with the thinner portion at the free first end of the elongate member received in the slot in the upstanding portion of the connecting member and the first mounting member and second mounting member engaging the first boss and the second boss and the first edge of the elongate member is nearest the first and second resection guide surfaces, a distance between the first edge and the plane of the first and second resection guide surfaces being a predetermined first distance; and a second orientation with the thinner portion at the free first end of the elongate member received in the slot in the upstanding portion of the connecting member and the first mounting member and second mounting member engaging the first boss and the second boss and the second edge of the elongate member is nearest the plane of the first and second resection guide surfaces, a distance between the first edge and the plane of the first and second resection guide surfaces being a predetermined second distance;

wherein the first predetermined distance is different from the second predetermined distance; and wherein the first predetermined distance and the second predetermined distance define an amount of bone to be resected from the patella.

7. A patella resection guide comprising a first arm, a second arm, a connecting member, a cooperative locking mechanism associated with the first arm and the second arm for releasably locking the first and second arms in a desired position, wherein:

each arm has a first end and a second end spaced from the first end;

each arm has a first portion extending from the first end and a second portion extending from the second end toward the first portion;

the first end of the first arm is pivotably connected to the connecting member about a first pivot axis;

the first end of the second arm is pivotably connected to the connecting member about a second pivot axis;

the first portion of the first arm is pivotably connected to the second portion of the first arm about a third pivot axis;

the first portion of the second arm is pivotably connected to the second portion of the second arm about a fourth pivot axis;

the first pivot axis, second pivot axis, third pivot axis and fourth pivot axis are parallel to each other;

the first portion of the first arm includes a first bone gripping member extending toward the first portion of the second arm;

the first portion of the second arm includes a second bone gripping member extending toward the first portion of the first arm;

the first bone-gripping member and second bone-gripping member lie in a plane that is substantially perpendicular to the first pivot axis, second pivot axis, third pivot axis and fourth pivot axis and define a space therebetween to receive a patella;

the first bone-gripping member and the second bone-gripping member are spaced apart by a distance;

the first arm includes a first planar resection guide surface substantially parallel to the plane of the first bone-gripping member;

the second arm includes a second planar resection guide surface substantially parallel to the plane of the first bone-gripping member;

pivoting the portions of the first and second arms about the first pivot axis, second pivot axis, third pivot axis and fourth pivot axis move the first bone-gripping member and second bone-gripping member toward and away from each other to vary the distance between the first bone-gripping member and the second bone-gripping member; and the second end of the first arm is pivotably connected to the second end of the second arm about a fifth pivot axis and the fifth pivot axis is parallel to the first pivot axis, second pivot axis, third pivot axis and fourth pivot axis.

8. The patella resection guide of claim 7 wherein the connections defining the first pivot axis, second pivot axis, third pivot axis, fourth pivot axis and fifth pivot axis comprising living hinges.

9. A patella resection guide comprising a first arm, a second arm, a connecting member, a cooperative locking mechanism associated with the first arm and the second arm for releasably locking the first and second arms in a desired position, wherein:

each arm has a first end and a second end spaced from the first end;

each arm has a first portion extending from the first end and a second portion extending from the second end toward the first portion;

the first end of the first arm is pivotably connected to the connecting member about a first pivot axis;

the first end of the second arm is pivotably connected to the connecting member about a second pivot axis;

the first portion of the first arm is pivotably connected to the second portion of the first arm about a third pivot axis;

the first portion of the second arm is pivotably connected to the second portion of the second arm about a fourth pivot axis;

the first pivot axis, second pivot axis, third pivot axis and fourth pivot axis are parallel to each other;

the first portion of the first arm includes a first bone gripping member extending toward the first portion of the second arm;

the first portion of the second arm includes a second bone gripping member extending toward the first portion of the first arm;

the first bone-gripping member and second bone-gripping member lie in a plane that is substantially perpendicular to the first pivot axis, second pivot axis, third pivot axis and fourth pivot axis and define a space therebetween to receive a patella;

the first bone-gripping member and the second bone-gripping member are spaced apart by a distance;

the first arm includes a first planar resection guide surface substantially parallel to the plane of the first bone-gripping member;

the second arm includes a second planar resection guide surface substantially parallel to the plane of the first bone-gripping member;

pivoting the portions of the first and second arms about the first pivot axis, second pivot axis, third pivot axis and fourth pivot axis move the first bone-gripping member and second bone-gripping member toward and away from each other to vary the distance between the first bone-gripping member and the second bone-gripping member;

the first planar resection guide surface is co-planar with the second planar resection guide surface;

the first arm, the second arm and connecting member comprise a unitary polymer base;

the first planar resection guide surface is part of an element distinct from and connected to the base;

the second planar resection guide surface is part of an element distinct from and connected to the base part;

the resection guide further comprises a first plate and a second plate;

the first plate is mounted to the base and positioned parallel to and spaced from the first planar resection guide surface to define a first guide slot; and the second plate is mounted to the base and positioned parallel to and spaced from the second planar resection guide surface to define a second guide slot.

10. The patella resection guide of claim 9 wherein the base extends from the first end to the second end of the first arm and from the from the first end to the second end of the second arm.

11. The patella resection guide of claim 10 wherein:
the first plate is pivotably connected to the base; and
the second plate is pivotably connected to the base.

12. The patella resection guide of claim 9 wherein:
the first planar resection guide surface comprises a channel member extending around part of the base and defining the first bone-gripping member; and
the second planar resection guide surface comprises a channel member extending around part of the base and defining the second bone-gripping member.

13. A patella resection guide comprising:
a first arm having a first end, a second end and a first bone-gripping member; and
a second arm having a first end, a second end and a second bone gripping member;
wherein:
the first arm and second arm are connected by a pivotal connection at the first end of the first arm and the first end of the second arm;
the first bone gripping member is between the pivotal connection and the second end of the first arm;
the second bone gripping member is between the pivotal connection and the second end of the second arm;
the first bone gripping member faces the second bone gripping member;
the first bone gripping member is spaced from the second bone gripping member;
at least part of the first bone gripping member is co-planar with at least part of the second bone gripping member;
at least one of the arms includes surfaces defining a resection guide slot lying in a plane parallel to the plane of the first bone gripping member and second bone gripping member; and
the first arm and second arm are movable to a variety of positions with different distances between the first bone-gripping member and the second bone-gripping member;
the first arm includes a base portion;
the second arm includes a base portion;
the first arm includes first planar resection guide surface distinct from and connected to the base portion of the first arm;
the second arm includes a second planar resection guide surface distinct from and connected to the base portion of the second arm;
the resection guide further comprises a first plate and a second plate;
the first plate is mounted on the base portion of the first arm and positioned parallel to and spaced from the first planar resection guide surface to define the guide slot; and
the second plate is mounted to the base portion of the second arm and positioned parallel to and spaced from the second planar resection guide surface to define a second guide slot;
the base portion of the first arm and the base portion of the second arm comprise a unitary polymer base.

14. The patella resection guide of claim 13 further comprising a connecting member pivotally connected to the first end of the first arm and the first end of the second arm, the connections between the first arm and the connecting member and between the second arm and the connecting member defining the pivotal connection between the first end of the first arm and the first end of the second arm.

15. The patella resection guide of claim 14 further comprising a stylus, wherein:
the connecting member includes an upstanding portion defining a through-slot;
the first arm includes a first upstanding boss having a central longitudinal axis;
the second arm includes a second upstanding boss having a central longitudinal axis parallel the central longitudinal axis of the first upstanding boss;
the stylus includes:
an elongate member having parallel first and second edges, a free first end and a second end and a thinner portion at the free first end; and
a cross-member having a first end, a second end, a central portion connected to the second end of the elongate member, a first end portion at the first end and a second end portion at the second end, the first end portion of the cross-member including a first mounting member and the second end portion of the cross-member including a second mounting member, the first mounting member and the second mounting member serving to selectively and removably mount the cross-member to the first upstanding boss and the second upstanding boss of the resection guide;
wherein the stylus is selectively and removably assembled with the resection guide with the thinner portion at the free first end of the elongate member received in the slot in the upstanding portion of the connecting member and the first mounting member and second mounting member engaging the first upstanding boss and the second upstanding boss; and
wherein when the stylus is assembled with the resection guide the first and second edges of the elongate member of the stylus are parallel to the planes surfaces defining the resection guide slot.

16. The patella resection guide of claim 15 wherein the stylus and resection guide can be assembled with the stylus being in one of two orientations, including:
a first orientation with the thinner portion at the free first end of the elongate member received in the slot in the upstanding portion of the connecting member and the first mounting member and second mounting member engaging the first upstanding boss and the second upstanding boss and the first edge of the elongate member is nearest the planes of the surfaces defining the resection guide slot, a distance between the first edge and the plane of the nearest surface defining the resection guide slot being a predetermined first distance; and a second orientation with the thinner portion at the free first end of the elongate member received in the slot in the upstanding portion of the connecting member and the first mounting member and second mounting member engaging the first upstanding boss and the second upstanding boss and the second edge of the elongate member is nearest the plane of the surfaces defining the resection guide slot, a distance between the first edge and the plane of the nearest surface defining the resection guide slot being a predetermined second distance;

wherein the first predetermined distance is different from the second predetermined distance; and wherein the first predetermined distance and the second predetermined distance define an amount of bone to be resected from the patella.

17. The patella resection guide of claim 15 wherein the stylus includes an additional cross-piece extending out perpendicularly from both sides of the elongate member.

18. The patella resection guide of claim 13 further comprising a locking mechanism extending between the first arm and the second arm to lock the first arm and the second arm in desired positions, wherein the first bone-gripping member is positioned between the locking mechanism and the pivotal connection and the second bone-gripping member is between the locking mechanism and the pivotal connection.

19. The patella resection guide of claim 18 wherein the locking mechanism comprises a ratchet and a ratchet locking plate, wherein:
the ratchet includes an end fixed to the first arm;
the second arm includes a ratchet slot; and
the ratchet extends from the first arm through the ratchet slot in the second arm.

20. The patella resection guide of claim 13 wherein:
the first arm comprises a plurality of portions linked together into a changeable configuration;
the second arm comprises a plurality of portions linked together into a changeable configuration;
the configurations of the linked portions of the first arm change as the first arm is moved to different positions; and
the configurations of the linked portions of the second arm change as the second arm is moved to different positions.

21. The patella resection guide of claim 20 wherein:
the links between portions of the first arm comprise hinges; and
the links between portions of the second arm comprise hinges.

22. The patella resection guide of claim 21 wherein:
the hinges of the first arm comprise living hinges; and
the hinges of the second arm comprise living hinges.

23. The patella resection guide of claim 13 wherein the base portion of the first arm and base portion of the second arm are connected by a connecting member.

24. The patella resection guide of claim 23 wherein:
the first plate is pivotably connected to the base portion of the first arm; and
the second plate is pivotably connected to the base portion of the second arm.

25. The patella resection guide of claim 24 wherein:
the first planar resection guide surface comprises a channel member extending around part of the base portion of the first arm and defines the first bone-gripping member; and
the second planar resection guide surface comprises a channel member extending around part of the base portion of the second arm and defines the second bone-gripping member.

26. The patella resection guide of claim 25 wherein:
the base portion of the first arm comprises a plurality of portions linked together into a changeable configuration;
the base portion of the second arm comprises a plurality of portions linked together into a changeable configuration;
the configurations of the linked portions of the base portion of the first arm change as the first arm is moved to different positions; and
the configurations of the linked portions of the base portion of the second arm change as the second arm is moved to different positions.

27. The patella resection guide of claim 26 wherein:
the links between portions of the base portion of the first arm comprise hinges; and
the links between portions of the base portion of the second arm comprise hinges.

28. The patella resection guide of claim 27 wherein:
the hinges of the base portion of the first arm comprise living hinges; and
the hinges of the base portion of the second arm comprise living hinges.

* * * * *

UNITED STATES PATENT AND TRADEMARK OFFICE
CERTIFICATE OF CORRECTION

| | | |
|---|---|---|
| PATENT NO. | : 8,821,501 B2 | Page 1 of 1 |
| APPLICATION NO. | : 13/176802 | |
| DATED | : September 2, 2014 | |
| INVENTOR(S) | : Maja Kecman et al. | |

It is certified that error appears in the above-identified patent and that said Letters Patent is hereby corrected as shown below:

On the Title page item (75) Inventors: please add, RUSTY T. MEIER

Signed and Sealed this
Fifteenth Day of September, 2015

Michelle K. Lee
*Director of the United States Patent and Trademark Office*